United States Patent [19]

Baumgartner

[11] Patent Number: 5,702,454
[45] Date of Patent: Dec. 30, 1997

[54] PROCESS FOR IMPLANTING AN INVERTEBRAL PROSTHESIS

[75] Inventor: Walter Baumgartner, Wil, Switzerland

[73] Assignee: Sulzer Orthopadie AG, Baar, Switzerland

[21] Appl. No.: 657,446

[22] Filed: May 29, 1996

Related U.S. Application Data

[62] Division of Ser. No. 223,489, Apr. 5, 1994.

[30] Foreign Application Priority Data

Apr. 21, 1993 [EP] European Pat. Off. .......... 93810291.0

[51] Int. Cl.⁶ .................. A61F 2/44; A61B 17/56
[52] U.S. Cl. ............................... 623/17; 606/61
[58] Field of Search ........................ 623/11, 17, 18, 623/16; 606/61; 128/898

[56] References Cited

U.S. PATENT DOCUMENTS

| | | | |
|---|---|---|---|
| 3,546,055 | 12/1970 | Spertus | 161/55 |
| 3,616,158 | 10/1971 | Rubens | 161/127 |
| 3,875,595 | 4/1975 | Froning | 3/1 |
| 3,933,959 | 1/1976 | Skochdopole et al. | 264/45.5 |
| 5,047,055 | 9/1991 | Bao et al. | 623/17 |
| 5,123,926 | 6/1992 | Pisharodi | 623/17 |
| 5,171,280 | 12/1992 | Baumgartner | 623/17 |
| 5,171,281 | 12/1992 | Parsons et al. | 623/17 |
| 5,181,614 | 1/1993 | Watts | 206/584 |
| 5,192,326 | 3/1993 | Bao et al. | 623/17 |
| 5,383,884 | 1/1995 | Summers | 606/170 |
| 5,383,888 | 1/1995 | Zvenyatsky et al. | 606/170 |
| 5,534,023 | 7/1996 | Henley | 623/11 |

FOREIGN PATENT DOCUMENTS

| | | |
|---|---|---|
| 1 146 301 | 5/1983 | Canada. |
| 0 304 305 | 8/1987 | European Pat. Off. .......... A61F 2/44 |
| 0 610 837 A1 | 2/1993 | European Pat. Off. .......... A61F 2/44 |
| 88 16184 | 12/1988 | France .......... A61F 2/44 |

*Primary Examiner*—Debra S. Brittingham
*Attorney, Agent, or Firm*—Townsend and Townsend and Crew LLP

[57] ABSTRACT

An implant consisting of several support members (7), which are produced from an elastic plastic, is provided as a replacement for a part, which is no longer capable of bearing loads, of the core region of an intervertebral disk (3). The support members (7) are inserted one after the other into a central cavity (5) constructed in the core region by means of a tube (6) passing through an outer annular region (4) of the intervertebral disk (3) until said cavity is filled. When the cavity (5) becomes clogged with the filling members (7), they become deposited on the boundary walls of the annular region (4) and against one another and are elastically deformed under stress. Accordingly a universal implant which can be adapted to cavities (5) of any shape, and which forms a relatively compact, elastic support structure, can be achieved.

11 Claims, 3 Drawing Sheets

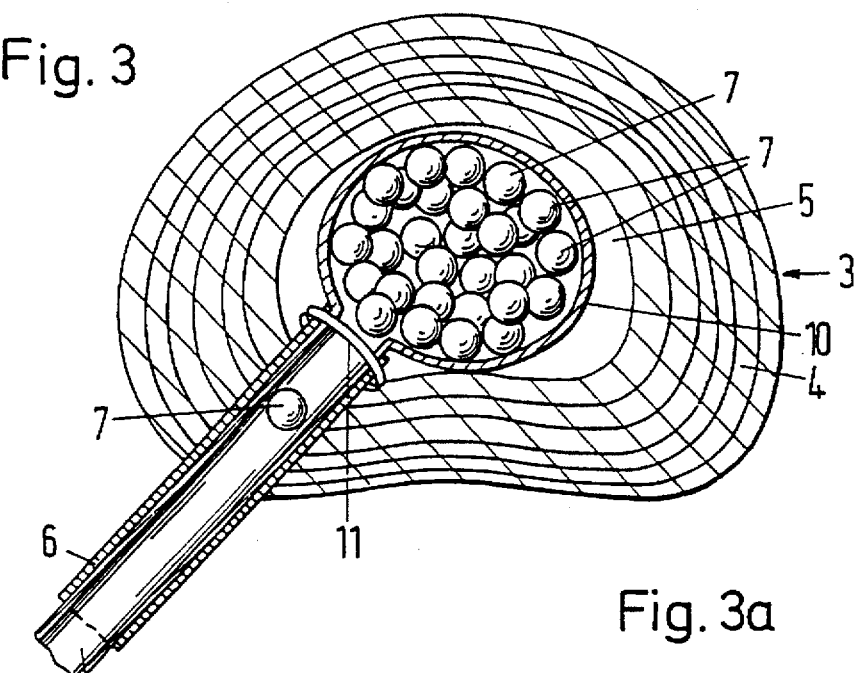
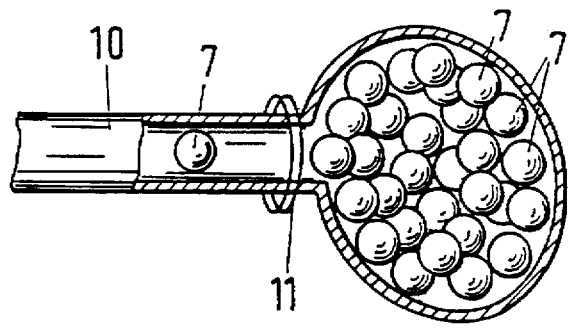
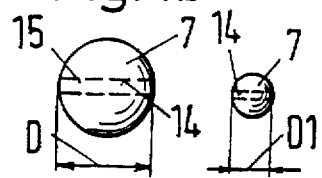
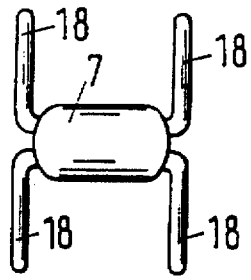
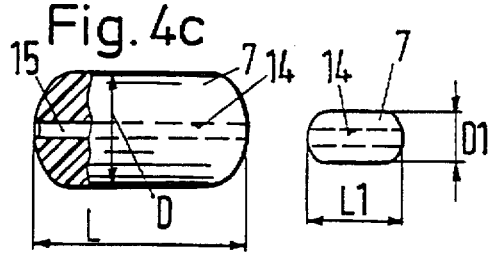
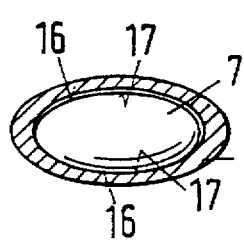
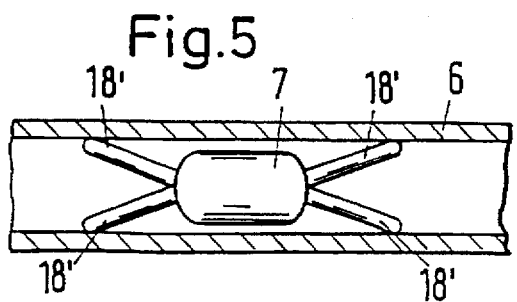

PROCESS FOR IMPLANTING AN INVERTEBRAL PROSTHESIS

RELATED U.S. APPLICATION DATA

This application is a division of U.S. application Ser. No. 08/223,489, filed Apr. 5, 1994, now pending.

FIELD OF THE INVENTION

The invention relates to an intervertebral prosthesis of the type having an implant for inserting into a central cavity of the core region of an intervertebral disk and also to a process for implanting such a prosthesis.

BACKGROUND OF THE INVENTION

Known intervertebral prostheses of the above mentioned type contain implants for intervertebral disks, which via a tube can be introduced through the outer ring (anulus fibrosus) of the intervertebral disk into its core region (nucleus pulposus), in order to achieve a bearing action in the direction of the main load. Thus, EP-A-0 453 393 shows a hollow member which can be introduced into the core region of the intervertebral disk, and which can be coiled in the shape of a spiral and which can be filled in the coiled state with an incompressible fluid. Before the insertion of such an implant, the core region of the intervertebral disk, which is no longer capable of bearing loads, has to be cleared out with auxiliary tools through the hollow tube, in order to replace the non-load-bearing material by the implant. As the surgeon has to work with predetermined implant sizes, he is forced to produce a matching cavity in the core region of the intervertebral disk. The known implant requires a relatively expensive design of the hollow member, in order to guarantee a permanent tightness against the egress of fluid, which is required if the implant is to work optimally.

SUMMARY OF THE INVENTION

The invention is intended to counteract these disadvantages.

The object of the invention is to create a universal, simple to apply implant, which can be used as a support member for varied cavities formed at random.

This object is achieved in accordance with the invention in that the implant contains at least three elastically deformable support members which can be inserted into the central cavity and can be positioned therein.

One advantage of the invention lies in that when creating the cavity, the surgeon only has to remove the material of the nucleus which is no longer capable of load bearing and that the quantity of support members to be inserted is necessarily established when the support members are inserted. The implant, which consists of support members which can be positioned spaced apart or touching one another and which can be made from an optional elastic material well tolerated by the body, is consequently suitable for every intervertebral disk. When the central cavity becomes clogged with the support members, they abut the boundary walls, so that a universal transfer of compressive forces and an optimal distribution in the central cavity can be achieved. During loading, the support members are elastically deformed, and the compressive forces acting in the direction of the member axis are converted into edge stresses in the anulus fibrosus.

According to a preferred embodiment according to the invention, the support members can be made from an elastic plastic. Accordingly an implant made from a suitable plastic material which can be well tolerated by the body, which can be manufactured with low expenditure and is permanently dimensionally stable, can be obtained.

The support members may preferably be designed in the form of rotational solids, which enable an optimal, uniform transfer of the compressive forces. In this respect spherical designs are particularly advantageous.

The packing density can be increased by the use of support members having different dimensions. By providing ducts in the support members, cavities can be produced, which in contrast to solid members, permit a defined, greater elastic deformation. In order to control the rigidity of the implant, a mixture of solid members and hollow members can be inserted. For the support members themselves there is a plurality of shapes, which ranges from the non-oriented spherical shape via lenticular and bean-shaped members to oblong, cylindrical, sausage-shaped members.

Several support members can be connected in chains to form a string-like, flexible support, whereby the distance between two support members advantageously corresponds at least to the diameter of one of the support members, in order to enable deviations of 180° when inserting the support members. Single-piece chains made from the same material are also possible, in which the flexible intermediate pieces are designed with a correspondingly thin shape. It is also possible to space support members with flexible tubing. The chain shape of the support members has firstly the advantage that a support member in a chain can not easily leave the central cavity through an aperture and secondly that during filling the operation can not be reversed without great time loss by withdrawing the chain. A similar retention action can be achieved on individual support members having elastically deformable expansion elements, which during insertion through the tube are deformed in the longitudinal direction and during entry into the central cavity spring back and assume a larger cross section.

A further method of depositing support members in a determined orientation lies in adapting the cross section of the tube to guide faces of the support members and depositing the support members purposefully—roughly like an insect laying its eggs—on determined sites of the central cavity, by the support member being guided in the tube and being ejected with a plunger. A lenticular member may be deposited so that, for example, its flat sides are directed against the adjacent vertebrae.

If the support members comprise a positional indicator, roughly in the form of an inclusion made from a material which is visible under X-ray examination, such as tantalum, for example, their depositing and subsequent changes in position can be controlled.

Polyurethane, for example, is suitable as the plastic for such support members. The support members may also be made from another material, e.g. a hydrogel. Corresponding support members may also be made from a suitable foam. Another design, in which each support member is formed by a cocoon-type coil consisting of a plastic thread or a metal thread, is also conceivable.

In order to increase the safety for the insertion and retention the support members, before the insertion of the support members a bag made from a synthetic woven fabric or plastic film can be introduced through the tube into the central cavity, whereby the aperture of the bag remains outside the tube. The support members are now inserted through the aperture of this bag, which aperture is supported on the tube. When the central cavity and the bag is filled with support members, the bag can be tied off with a clamp or wire, in order to prevent support members coming out.

BRIEF DESCRIPTION OF THE DRAWINGS

Further features and details can be gathered from the following description of exemplified embodiments of the invention, in conjunction with the claims, represented diagrammatically in the drawings.

FIG. 3 shows a cross section through an intervertebral disk, having an implant in a modified embodiment:

FIG. 3a shows a cross section through a bag with support members;

FIG. 4a–4e show various embodiments of support members constructed in accordance with the invention;

FIG. 5 shows the support member shown in FIG. 4e in a position during insertion through a tube represented in a partial longitudinal section;

DESCRIPTION OF THE PREFERRED EMBODIMENTS

Figure 1:
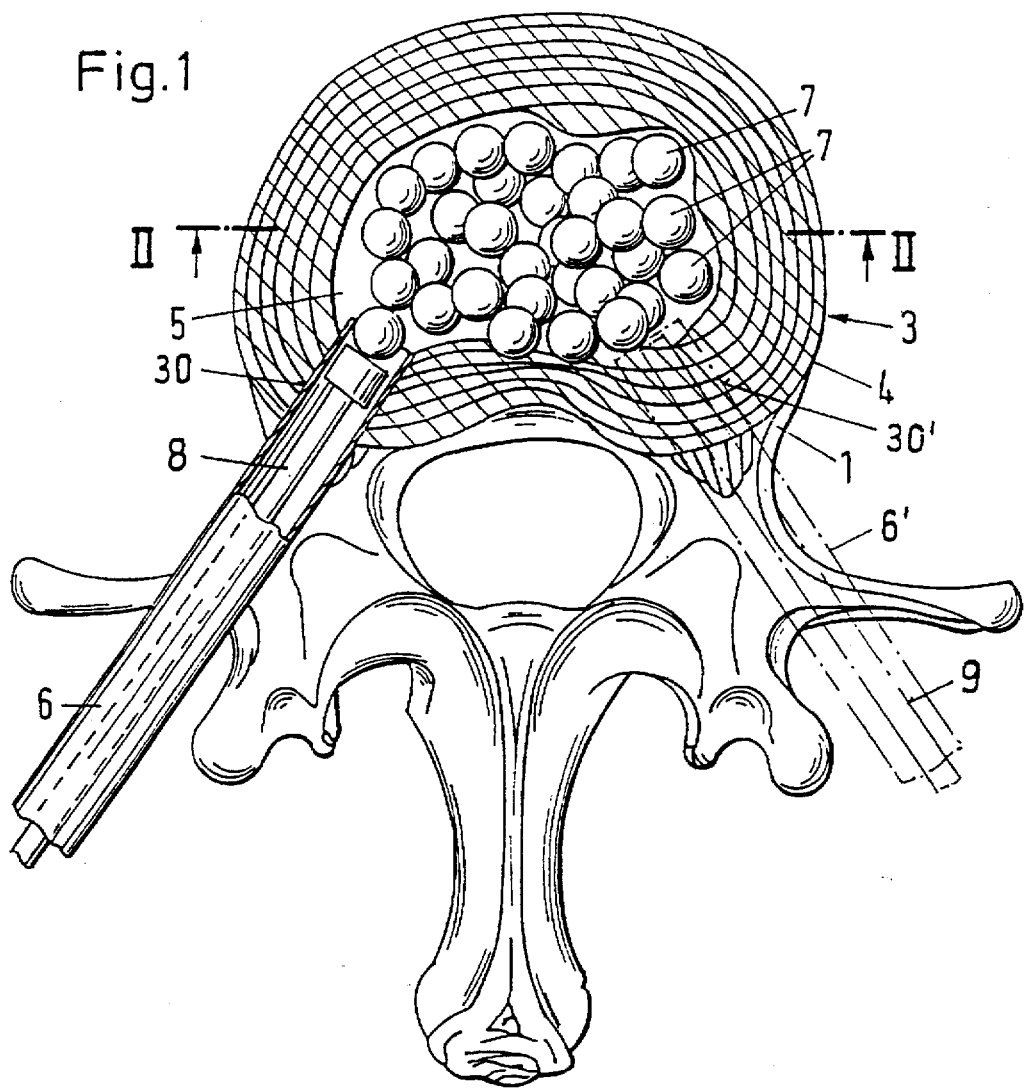
FIG. 1 shows a body of a vertebra in a plan view with a cross section through an intervertebral disk, which contains an implant of support members, which can be supplied via a tube.
Figure 2:
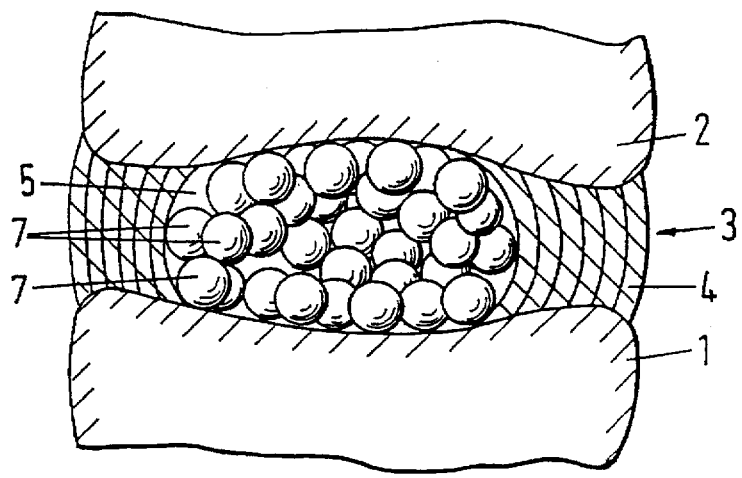
FIG. 2 shows the intervertebral disk in a longitudinal section takes along line II—II in FIG. 1.

As shown in FIGS. 1 and 2, an intervertebral disk 3 positioned between two vertebral bodies 1 comprises an intact outer annular region 4 of natural tissue, which surrounds a central core region. In the core region is formed a cavity 5, which was previously created by the removal of the core of the damaged intervertebral disk—or a part thereof—and if necessary damaged parts of the outer annular region 4. The formation of the cavity 5 and the removal of the tissue parts which are no longer capable of load-bearing is performed in a known manner by a tubular guide part, as represented in the form of a tube 6, which, as for example in EP-A-0 453 393 mentioned at the beginning, is inserted, passing through an aperture 30 in the outer annular region 4, into the core region of the intervertebral disk 3 by a relatively slight engagement from the dorsal side between the vertebral bodies 1 and 2. A gouge is inserted into the core region through the inserted tube 6, by which the cavity 5 is created and the cut out tissue parts are removed.

An intervertebral prosthesis in the form of an implant consisting of several support members 7, which can be inserted one after the other into the cavity 5, and which are made from an elastic plastic well tolerated by the body, e.g. polyurethane, is provided as a replacement for at least one part of the core region removed. The support members 7 are constructed as rotational solids, and in the example represented in the form of balls, the dimensions of which are chosen so that they can be inserted through the tube 6 into the cavity 5. The support members 7 are packed into the cavity 5, if necessary by means of a plunger 8, until the cavity is substantially filled by the support members 7 resting against one another and the support members 5 form a new core region of the intervertebral disk 3 capable of the transfer of compressive forces. The number and dimensions of the support members 7 can be varied at random according to the dimensions given and the shape of the cavity 5 to be filled and the cross section of the tube 6. Thus, for example, a design is possible which requires fewer support members 7 than the design shown, e.g. three support members 7 designed in appropriate sizes. The support members 7 can be designed with varying dimensions or, as represented, with the same diameters. A design is also possible with support members 7 disposed in a single layer, for example, which can be disposed at a distance or at varying distances from one another.

The tube 6 is withdrawn in a known manner from the annular region 4, whereby the through-duct—aperture 30—for the tube 6 is closed accordingly in front of the last support member 7 inserted. This may be provided, in a manner still to be described, with retention means which make it difficult for support member to leave through the through-channel.

An observation instrument 9 can be inserted through the tube 6' to monitor the clearing of the cavity 5 and/or the implantation operation or an auxiliary instrument (not represented) can be inserted to assist the clearing and implantation process. It is obvious that instead of the tubes 6, 6' represented, other suitable protective and/or guide elements of any shape and design can also be used.

In FIG. 3 the corresponding parts are provided with the same reference numbers. According to this embodiment the support members 7 can be disposed in a surrounding covering, such as a bag 10, which is inserted in the empty state through the tube 6 into the cavity 5 and then filled with the support members 7 through the aperture remaining outside the tube 6. The bag 10 may be made from a woven fabric, a knitted fabric or a film made from an elastic plastic well tolerated by the body, e.g., polyethylene. When the bag 10 is filled and is connected to the support members 7 to form a compact, elastic implant suitable for transmitting compressive forces between the vertebral bodies 1 and 2, the bag 10 can be tied off by a sealing part 11, e.g. in the form of a clamp or, as shown in the drawings, a previously inserted wire loop, in order to keep the support members 7 together. After this, the end of the bag 10 is cut off and withdrawn together with the tube 6.

As can be seen in particular from FIG. 3a, the bag 10 can be adapted to any desired shape of the cavity 5 to be filled according to the prevailing anatomical conditions.

Numerous embodiments of support member 7 are possible. Thus, for example, instead of rotational solids, designs with polyhedral support members 7 are possible. As shown in FIG. 4a, the spherical support members 7 in the design represented—or at least one or some of the support members 7—may be designed with a closed cavity 12, which contain an insert 13 in the form of a spherical inclusion made from a material which is visible under X-ray examination, e.g. tantalum, as a positional indicator for the respective position of the support members 7. Designs without an insert 13 are possible, in which case a correspondingly greater elastic deformation of the support member can be achieved by the cavity 12.

As shown in FIG. 4b, at least some of the support members 7 may have different diameters D or D1 and/or are designed with a duct 14 passing through them, which is open, or as represented can be provided with a rod-shaped insert 15 as a positional indicator, whereby the respective orientation of the insert 15 can be seen.

As shown in FIG. 4c, support members 7 can be designed with substantially cylindrical shapes rounded off at the ends, which can also be provided with a duct 14 and/or with a rod-shaped inclusion 15—or for example with two corresponding inclusions, offset against one another in the axial direction of the support member 7. These support members 7 may also have different diameters D or D1 and/or different lengths L or L1.

As shown in FIG. 4d, at least some of the support members 7 can be lenticular, and in the example represented, in the shape of an ellipsoid, and can be accordingly designed with defined support surfaces 16, which permit the support members 7 to be deposited purposefully with the support faces 16 directed against the adjacent vertebral bodies 1, 2. As can also be seen from FIG. 4d, the tube 6 can be designed with a corresponding cross section, which as represented is oval, and which forms guideways 17 for the support faces 16.

As shown in FIG. 4e, at least one of the support members, e.g. the last support member 7 to be inserted into the cavity 5, can be provided with at least one, and as shown four elastically deformable expansion elements 18, which in the expanded state protrude laterally from the support member 7 and which, as represented in FIG. 5, are deformed when inserted through the tube 6 in the longitudinal direction into stressed positions 18' and spring back, on leaving the tube 6, inside the cavity 5 in the expanded state, and thus prevent the support members from leaving the cavity 5 through the through-aperture for the tube 6.

Figure 6:
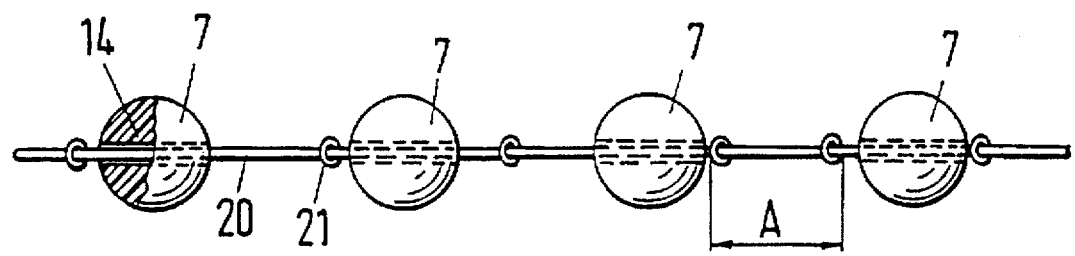
FIG. 6, 7 and 8 show implants consisting of several support members connected to one another, in different embodiments.

As can be seen from FIG. 6, several support members can be disposed in the manner of pearls on a pearl necklace on a flexible, ribbon-like or string-like support 20 and be connected thereto to form a cohesive implant. The support 20 may preferably be provided with stop parts 21 disposed between the support members 7, as represented in the form of knots constructed on the support 20, so that a predetermined minimum distance A is observed between the support members 7, which corresponds at least approximately to the diameter of one of the support members 7 or—in designs in which the dimensions of the support members 7 vary—the sum of the radii of the adjacent support members 7.

Figure 7:
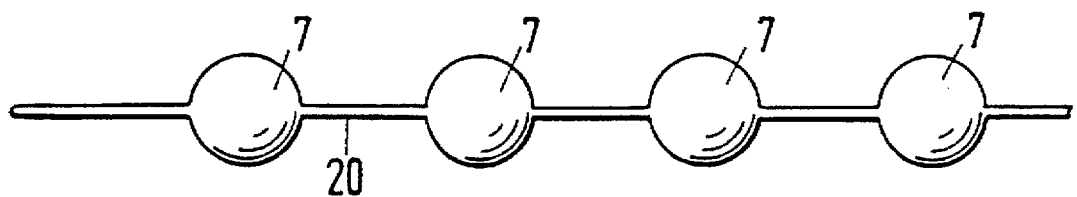
Figure 8:
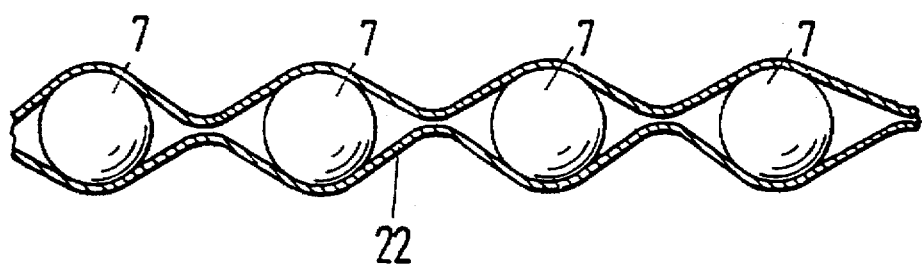

As shown in FIG. 7, the support members 7 and the support 20 are manufactured from the same material and are connected to form a single-piece implant, whereby the support 20 acts as a spacer. According to the representation shown in FIG. 8, a number of support members 7 can be disposed in a covering in the form of tubing 22 tightly surrounding the support members 7 and can be connected thereto to form a cohesive implant. The tubing 22, just like the bag 10, may be formed from a corresponding woven fabric, a knitted fabric or a film.

In summary, the invention can be described as follows:

An implant consisting of several support members 7, which are produced from an elastic plastic, is provided as a replacement for a part of the core region of an intervertebral disk 3 which is no longer capable of load bearing. The support members 7 are sequentially inserted into a central cavity 5 constructed in the core region by means of a tube 6 passing though an outer annular region 4 of the intervertebral disk 3, until said cavity is substantially filled. When the cavity 5 is clogged with the filling members 7, they become deposited at the boundary walls of the annular region 4 and against one another and are elastically deformed under stress. Accordingly, a universal implant which can be adapted to cavities 5 of any shape, and which forms a relatively compact, elastic support structure, can be achieved.

I claim:

1. A method for implanting an intervertebral prosthesis comprising:

forming a cavity within an intervertebral disc;

providing at least three elastically deformable support members;

individually introducing each of the support members into the cavity of the intervertebral disc; and individually positioning each of the support members within the cavity of the intervertebral disc.

2. The method of claim 1 further comprising forming an opening through an outer wall of the intervertebral disc.

3. The method of claim 2 wherein the forming step comprises removing tissue from a core of the intervertebral disc to form the cavity therein.

4. The method of claim 2 further comprising closing the opening after the support members have been positioned within the central cavity.

5. The method of claim 1 wherein the introducing step is carried out by forming an opening in an outer wall of the intervertebral disc, introducing a distal end of a hollow tube through the opening and delivering the support members through the tube into the cavity.

6. The method of claim 5 further comprising forming a second opening in the outer wall of the intervertebral disc and introducing a distal end of the second hollow tube through the second opening.

7. The method of claim 6 further comprising introducing a viewing scope through the distal end of the second hollow tube and monitoring the cavity during the support member introducing step.

8. The method of claim 6 further comprising introducing an instrument through the distal end of the second hollow tube and positioning at least one of the support members within the cavity with the instrument.

9. The method of claim 5 further comprising:

introducing a thin membrane into the cavity, the membrane defining an inner cavity and having an opening aligned with the distal end of the tube; and delivering the support members through the tube and the membrane opening into the inner cavity of the membrane.

10. The method of claim 5 wherein the support members are mounted and spaced on an elongate flexible support, the method further comprising advancing the support through the tube and delivering the support members into the cavity one at a time.

11. A method for implanting an intervertebral prosthesis comprising:

forming a cavity within an intervertebral disc;

providing at least three elastically deformable support members; and sequentially introducing each of the support members one at a time into the cavity of the intervertebral disc.

* * * * *